United States Patent
Peumans et al.

(10) Patent No.: US 9,599,509 B2
(45) Date of Patent: Mar. 21, 2017

(54) SPECTROSCOPY SYSTEM WITH DISPLACEMENT COMPENSATION AND SPECTROSCOPY METHOD USING THE SPECTROSCOPY SYSTEM

(71) Applicants: SAMSUNG ELECTRONICS CO., LTD., Suwon-si (KR); IMEC VZW, Leuven (BE)

(72) Inventors: Peter Peumans, Herne (BE); Seongho Cho, Gwacheon-si (KR); Woochang Lee, Anyang-si (KR)

(73) Assignees: SAMSUNG ELECTRONICS CO., LTD., Suwon-si (KR); IMEC VZW, Leuven (BE)

( * ) Notice: Subject to any disclaimer, the term of this patent is extended or adjusted under 35 U.S.C. 154(b) by 0 days.

(21) Appl. No.: 14/934,722

(22) Filed: Nov. 6, 2015

(65) Prior Publication Data

US 2016/0131523 A1   May 12, 2016

(30) Foreign Application Priority Data

Nov. 7, 2014   (KR) ..................... 10-2014-0154735

(51) Int. Cl.
| | |
|---|---|
| G01N 21/00 | (2006.01) |
| G01J 3/02 | (2006.01) |
| G01J 3/44 | (2006.01) |
| A61B 5/00 | (2006.01) |
| G01N 21/359 | (2014.01) |
| G01N 21/65 | (2006.01) |
| A61B 5/11 | (2006.01) |

(Continued)

(52) U.S. Cl.
CPC .......... *G01J 3/0289* (2013.01); *A61B 5/0059* (2013.01); *A61B 5/0075* (2013.01); *A61B 5/11* (2013.01); *A61B 5/14532* (2013.01); *A61B 5/441* (2013.01); *G01J 3/28* (2013.01); *G01J 3/44* (2013.01); *G01N 21/359* (2013.01); *G01N 21/65* (2013.01); *A61B 5/721* (2013.01); *A61B 2562/0233* (2013.01); *A61B 2562/04* (2013.01)

(58) Field of Classification Search
CPC . G01N 21/65; G01N 21/51; G01J 3/02; G01J 3/44
USPC ............................................ 356/72–73, 301
See application file for complete search history.

(56) References Cited

U.S. PATENT DOCUMENTS

| | | |
|---|---|---|
| 7,034,945 B2 | 4/2006 | Kendrick et al. |
| 7,973,937 B1 | 7/2011 | Kendrick et al. |
| 8,787,630 B2 | 7/2014 | Rowe |

(Continued)

FOREIGN PATENT DOCUMENTS

| | | |
|---|---|---|
| JP | 3443688 B2 | 9/2003 |
| JP | 2013-228322 A | 11/2013 |
| WO | 2015/017623 A1 | 2/2015 |

OTHER PUBLICATIONS

Communication issued Apr. 14, 2016, issued by the European Patent Office in counterpart European Patent Application No. 15193113.6.

*Primary Examiner* — Abdullahi Nur
(74) *Attorney, Agent, or Firm* — Sughrue Mion, PLLC (57) ABSTRACT

A spectroscopy system includes detectors configured to obtain detection spectrums of respective detection areas that are located at different positions of an object; and an information processor configured to obtain a target spectrum of a target area by using position information of the detection areas and the detection spectrums obtained by the detectors.

20 Claims, 5 Drawing Sheets

(51) Int. Cl.
  *A61B 5/145*  (2006.01)
  *G01J 3/28*  (2006.01)

(56) References Cited

U.S. PATENT DOCUMENTS

| | | |
|---|---|---|
| 2006/0181543 A1 | 8/2006 | Katsumata et al. |
| 2007/0002276 A1 | 1/2007 | Hirohara et al. |
| 2007/0081156 A1 | 4/2007 | Treado et al. |
| 2014/0097359 A1* | 4/2014 | Vasic ................. G01N 21/6408 250/459.1 |
| 2014/0253924 A1 | 9/2014 | Sano |

* cited by examiner

SPECTROSCOPY SYSTEM WITH DISPLACEMENT COMPENSATION AND SPECTROSCOPY METHOD USING THE SPECTROSCOPY SYSTEM

CROSS-REFERENCE TO RELATED APPLICATION

This application claims priority from Korean Patent Application No. 10-2014-0154735, filed on Nov. 7, 2014, in the Korean Intellectual Property Office, the disclosure of which is incorporated herein in its entirety by reference.

BACKGROUND

1. Field

Apparatuses and methods consistent with exemplary embodiments relate to displacement compensation in spectroscopy.

2. Description of the Related Art

A technology for analyzing the skin by using spectroscopy has used fixed focus and fixed detection areas in order to reduce measurement error and to secure reproducibility. Accordingly, if a foreign substance such as a strand of hair or a sweat gland, which makes detection difficult, is present in a specific portion of the skin, the skin is measured again after changing the position of the detection area.

Recently, with the micro-miniaturization of near-infrared spectrometers and Raman spectrometers, near-infrared spectrometers or Raman spectrometers are being more widely applied and a technology allowing users to conveniently perform measurements has been developed. A technology for performing measurements on a biological sample such as the skin by using a microminiaturized spectrometer may dramatically increase the measurement range and the number of measurements that can be made in comparison to a related art technology that is only able to perform measurements at limited positions or in a limited area. However, when such a microminiaturized spectrometer is mounted on a moving body part such as a wrist or an elbow, a relative position of the microminiaturized spectrometer may change as time passes.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide spectroscopy systems with displacement compensation and spectroscopy methods using the spectroscopy systems.

According to an aspect of an exemplary embodiment, a spectroscopy system includes: a plurality of detectors that obtain detection spectrums of a plurality of detection areas that are located at different positions of an object; and an information processor that obtains a target spectrum of a desired target area by using position information of the plurality of detection areas and the detection spectrums obtained by the plurality of detectors.

As the object moves, a relative position of at least one of the plurality of detection areas with respect to the target area may change. The information processor may calculate the target spectrum by linearly combining relative position information of the plurality of detection areas with respect to the target area with the detection spectrums. The spectroscopy system may further include at least one displacement sensor that is configured to measure displacements of the plurality of detection areas.

Each of the plurality of detection areas may include a three-dimensional (3D) area that extends from a surface of the object to a predetermined depth. The plurality of detection areas may include at least three detection areas that are two-dimensionally arranged. The plurality of detection areas may be spaced apart from one another or partially overlap with one another. The plurality of detectors may simultaneously or sequentially measure the detection spectrums of the plurality of detection areas.

The plurality of detectors may measure the detection spectrums by using Raman spectroscopy or near-infrared spectroscopy. Each of the plurality of detectors may be provided adjacent to a surface of the object, and includes an aperture via which the detector receives an optical signal output from each of the plurality of detection areas of the object.

According to an aspect of another exemplary embodiment, a spectroscopy method includes: obtaining detection spectrums of a plurality of detection areas that are located at different positions by using a plurality of detectors; obtaining position information of the plurality of detection areas; and obtaining a target spectrum of a desired target area by using the position information of the plurality of detection areas and the detection spectrums obtained by the plurality of detectors.

The spectroscopy method may further include analyzing an analyte of the object that is located in the desired target area from the target spectrum.

As the object moves, a relative position of at least one of the plurality of detection areas with respect to the target area may change. The obtaining of the target spectrum may include linearly combining relative position information of the plurality of detection areas with respect to the target area with the detection spectrums. The position information of the plurality of detection areas may be obtained by using at least one displacement sensor.

Each of the plurality of detection areas may include a 3D area that extends from a surface of the object to a predetermined depth. The plurality of detection areas may include at least three detection areas that are two-dimensionally arranged. The plurality of detection areas may be spaced apart from one another or partially overlap with one another. The obtaining of the plurality of detectors may include simultaneously or sequentially measuring the detection spectrums of the plurality of detection areas.

BRIEF DESCRIPTION OF THE DRAWINGS

The above aspects and/or other aspects will become more apparent by describing certain exemplary embodiments with reference to the accompanying drawings, in which.

DETAILED DESCRIPTION

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

Figure 1:
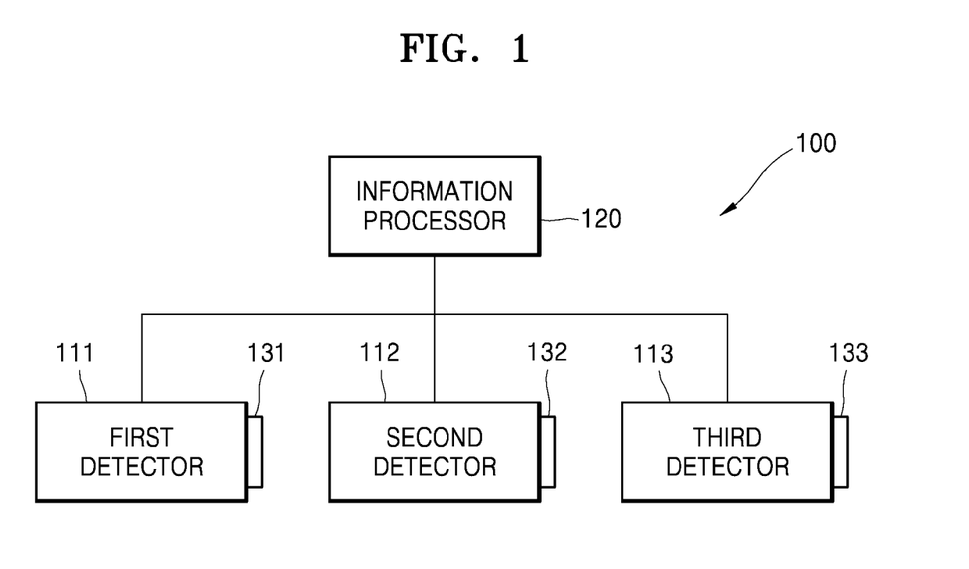
FIG. 1 is a block diagram illustrating a spectroscopy system according to an exemplary embodiment.

Referring to FIG. 1, the spectroscopy system 100 includes a plurality of detectors, e.g., first, second, and third detectors 111, 112, and 113, and an information processor 120, according to an exemplary embodiment.

Figure 2:
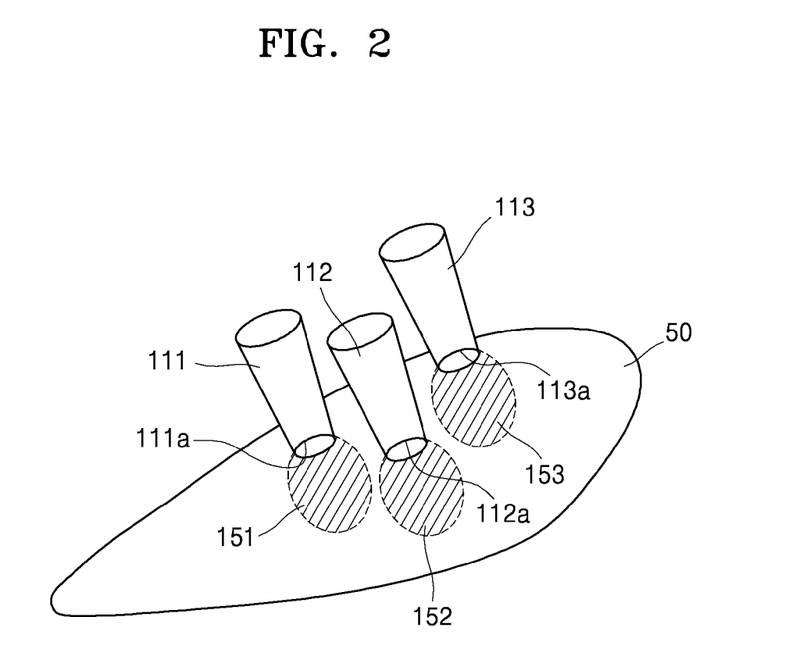
FIG. 2 is a view illustrating a state in which detectors of the spectroscopy system of FIG. 1 are provided on detection areas of an object, according to an exemplary embodiment.

With further reference to FIG. 2, the first through third detectors 111, 112, and 113 may obtain detection spectrums of a plurality of detection areas, e.g., first, second, and third detection areas 151, 152, and 153, that are located at different positions of an object 50. Each of the first through third detection areas 151, 152, and 153 may be a 3D area having a predetermined shape that extends from a surface of the object 50 to a predetermined depth. As time passes and the object 50 moves, positions of the first through third detection areas 151, 152, and 153 may change. For example, when the object 50 is a biological sample, tissue, or an organ, for example, a skin of a human, the object 50 may move as time passes, and thus the positions of the first through third detection areas 151, 152, and 153 may be changed. Since the first through third detectors 111, 112, and 113 may be provided to contact the surface of the object 50, the first through third detectors 111, 112, and 113 may move along with the first through third detection areas 151, 152, and 153 as the object 50 moves.

The first through third detectors 111, 112, and 113 may obtain the detection spectrums of the first through third detection areas 151, 152, and 153 that are formed in the object 50 by using Raman spectroscopy or near-infrared spectroscopy. The first through third detectors 111, 112, and 113 may simultaneously detect the detection spectrums of the first through third detection areas 151, 152, and 153 or may sequentially detect the detection spectrums of the first through third detection areas 151, 152, and 153 at predetermined time intervals. An analyte in each of the first through third detection areas 151, 152, and 153 may be analyzed from the detection spectrums. For example, when the object 50 is a biological sample such as the skin of a human, concentrations of blood glucose or the like in the first through third detection areas 151, 152, and 153 may be analyzed from the detection spectrums that are obtained by the first through third detectors 111, 112, and 113. Although the spectroscopy system 100 includes three detectors, that is, the first through third detectors 111, 112, and 113 in FIG. 1, an exemplary embodiment is not limited thereto and the spectroscopy system 100 may include a various number of detectors. In detail, the spectroscopy system 100 may include three or more detectors, and the detectors may be two-dimensionally arranged.

Figure 3:
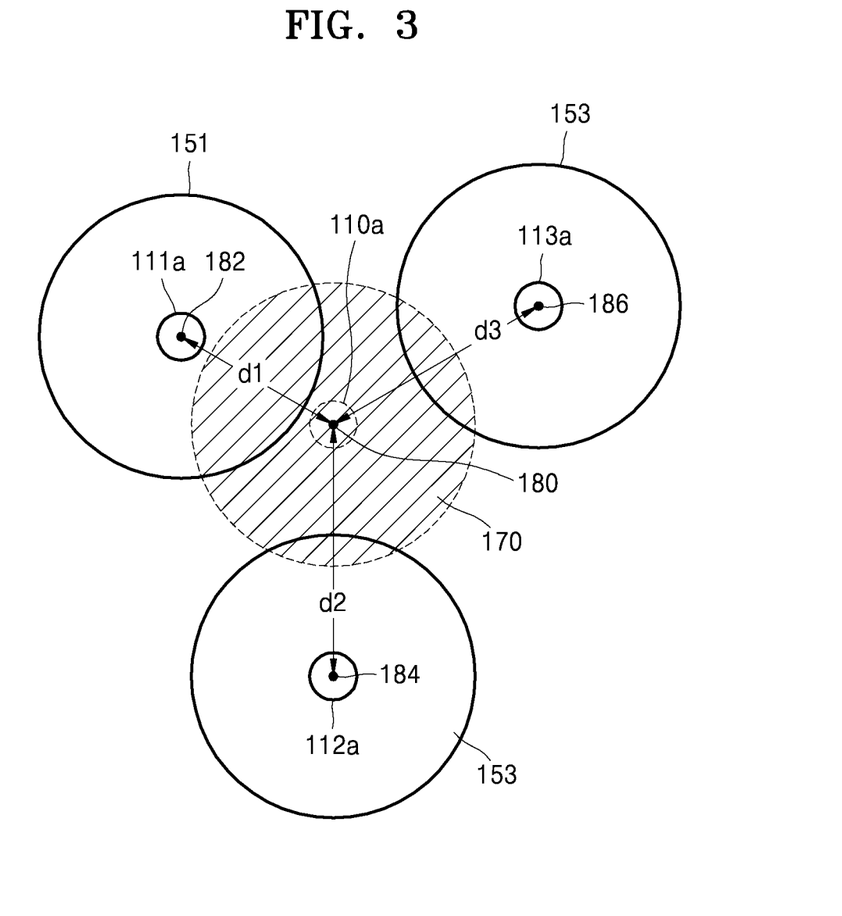
FIG. 3 is a plan view illustrating a state in which the detection areas and a target area are arranged, according to an exemplary embodiment.

With further reference to FIG. 3, the information processor 120 may obtain a target spectrum of a target area 170 by using position information of the first through third detection areas 151, 152, and 153 and the detection spectrums obtained by the first through third detectors 111, 112, and 113. The target area 170 is an area that is formed at a specific position of the object 50 to be measured. A position of the target area 170 is not changed as the object 50 moves, unlike the first through third detection areas 151, 152, and 153. However, when the specific position to be measured is changed, the position of the target area 170 may be changed. The information processor 120 may calculate the target spectrum of the target area 170 at a specific point of time by linearly combining relative position information of the first through third detection areas 151, 152, and 153 with respect to the target area 170 with the detection spectrums obtained by the first through third detectors 111, 112, and 113 as described in detail below. An analyte of the object 50 at the specific position to be measured may be analyzed from the calculated target spectrum.

With continuing reference to FIG. 1, the spectroscopy system 100 may further include a plurality of displacement sensors, e.g., first, second, and third displacement sensors 131, 132, and 133, to effectively obtain the position information of the first through third detection areas 151, 152, and 153. The first through third displacement sensors 131, 132, and 133 may obtain the relative position information of the first through third detection areas 151, 152, and 153 with respect to the target area 170 by sensing movements of the first through third detectors 111, 112, and 113. In detail, as time passes and the object 50 moves, the first through third displacement sensors 131, 132, and 133 may measure displacements of the first through third detection areas 151, 152, and 153 with respect to the target area 170 at the specific point of time by sensing the movements of the first through third detectors 111, 112, and 113. Accordingly, the first through third displacement sensors 131, 132, and 133 may obtain the relative position information of the first through third detection areas 151, 152, and 153 with respect to the target area 170 at the specific point of time. Examples of the first through third displacement sensors 131, 132, and 133 may include optical displacement sensors, capacitive displacement sensor, electromagnetic displacement sensors, and various other displacement sensors.

A case where three displacement sensors, that is, the first through third displacement sensors 131, 132, and 133, are respectively provided on three detectors, that is, the first through third detectors 111, 112, and 113, is illustrated in FIG. 1 as an example only. However, an exemplary embodiment is not limited thereto, and the first through third displacement sensors 131, 132, and 133 may be provided to be spaced apart from the first through third detectors 111, 112, and 113 and a number of the displacement sensors may be less than three or greater than three. For example, at least one displacement sensor may be provided to be spaced apart from the first through third detectors 111, 112, and 113 and may sense the movements of the first through third detectors 111, 112, and 113.

Referring again to FIGS. 2 and 3, the first through third detectors 111, 112, and 113 may be provided to contact the object 50. The object 50 may include, but is not limited to, a biological sample, such as the skin of a human, whose surface may move as time passes.

The first through third detectors 111, 112, and 113 may include first, second, and third apertures 111a, 112a, and 113a that are formed to contact the first through third detection areas 151, 152, and 153 of the object 50. Light emitted from a light source (not shown) that is provided on the first detector 111 may be incident on the surface of the object 50 through the first aperture 110a, and thus an optical signal output from the first detection area 151 that extends from the surface of the object 50 to the predetermined depth may be received by the first detector 111 through the first aperture 110a. The first detector 111 may detect the first detection spectrum of the first detection area 151 of the object 50 by using the optical signal that is received through the first aperture 111a. The second detector 112 may detect the second detection spectrum of the second detection area 152 of the object 50 by using an optical signal received through the second aperture 112a, and the third detector 113 may detect the third detection spectrum of the third detection area 153 of the object 50 by using an optical signal received through the third aperture 113a.

The first through third detection areas 151, 152, and 153 may be arranged, for example, two-dimensionally. Each of the first through third detection areas 151, 152, and 153 may be a 3D area that extends from the surface of the object 50 to the predetermined depth. When the object 50 is the skin of a human, as time passes, the object 50 may move. In this case, a position of at least one of the first through third detection areas 151, 152, and 153 may be changed as the object 50 moves.

FIG. 3 illustrates the first through third detection areas 151, 152, and 153 and the target area 170 of the object 50 at an arbitrary point of time. Referring to FIG. 3, the first through third detection areas 151, 152, and 153 are located at different positions of the object 50. Although the first through third detection areas 151, 152, and 153 are exemplarily provided to be spaced apart from one another in FIG. 3, at least one of the first through third detection areas 151, 152, and 153 may be provided to partially overlap with other detection areas. The first through third detection areas 151, 152, and 153 may be respectively provided to have predetermined shapes respectively about the first through third apertures 111a, 112a, and 113a. The target area 170 that is located at the specific position of the object 50 to be measured may be provided, but is not limited to, between the first through third detection areas 151, 152, and 153.

As shown in FIG. 3, in a state in which the first through third detection areas 151, 152, and 153 are two-dimensionally arranged, the target spectrum of the target area 170 that is located at the specific position to be analyzed may be derived by using the relative position information of the first through third detection areas 151, 152, and 153 with respect to the target area 170 and the first through third detection spectrums of the first through third detection areas 151, 152, and 153. The relative position information of the first through third detection areas 151, 152, and 153 with respect to the target area 170 may be determined by distances d1, d2, and d3 between a center point 180 of the target area 170 and center points 182, 184, and 186 of the first through third detection areas 151, 152, and 153. Reference numeral 110a in FIG. 3 denotes a virtual aperture that is virtually formed to correspond to the target area 170.

Figure 4:
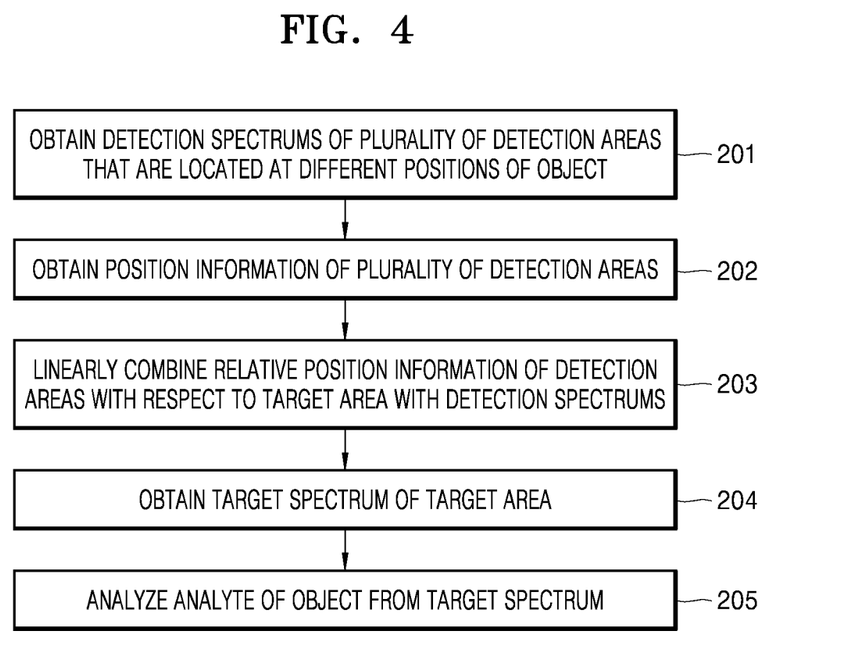
FIG. 4 is a flowchart of a spectroscopy method of analyzing an analyte of the object in the target area by using the spectroscopy system of FIG. 1, according to an exemplary embodiment.

FIG. 4 is a flowchart of a spectroscopy method of analyzing an analyte of the object 50 by using the spectroscopy system 100 of FIG. 1, according to an exemplary embodiment. The above-described embodiments of FIGS. 1, 2, and 3 are applicable in an exemplary embodiment of FIG. 4.

Referring to FIG. 4, in operation 201, detection spectrums of the plurality of detection areas, that is, the first through third detection areas 151, 152, and 153 that are located at different positions are obtained. In detail, first through third detection spectrums of the first through third detection areas 151, 152, and 153 that are located at different positions of the object 50 in FIG. 3 are detected by the first through third detectors 111, 112, and 113.

In operation 202, position information of the first through third detection areas 151, 152, and 153 is obtained. Relative position information of the first through third detection areas 151, 152, and 153 with respect to the target area 170 may be obtained by using the first through third displacement sensors 131, 132, and 133. The relative position information of the first through third detection areas 151, 152, and 153 with respect to the target area 170 may be determined by the distances d1, d2, and d3 between the target area 170 and the first through third detection areas 151, 152, and 153.

The information processor 120 calculates a target spectrum of the target area 170 that is located at a specific position to be analyzed by using the relative position information of the first through third detection areas 151, 152, and 153 with respect to the target area 170 and the first through third detection spectrums.

In detail, in operation 203, the information processor 120 linearly combines the relative position information of the first through third detection areas 151, 152, and 153 with respect to the target area 170 with the first through third detection spectrums.

In operation 204, the information processor 120 calculates the target spectrum of the target area 170.

The target spectrum of the target area 170 may be calculated by using the following Equation 1:

$$ST = \alpha \times S1 + \beta \times S2 + \gamma \times S3 \qquad (1),$$

where ST is the target spectrum of the target area 170,
S1, S2, and S3 are respectively the first through third detection spectrums,
α is a first contribution rate at which the first detection spectrum S1 contributes to the target spectrum ST,
β is a second contribution rate at which the second detection spectrum S2 contributes to the target spectrum ST, and
γ is a third contribution rate at which the third detection spectrum S3 contributes to the target spectrum ST, and $$\alpha + \beta + \gamma = 1.$$

The contribution rates α, β, and γ may be determined by the relative position information of the first through third detection areas 151, 152, and 153 with respect to the target area 170. In detail, the contribution rates α, β, and γ may be determined between the distances d1, d2, and d3 between the target area 170 and the first through third detection areas 151, 152, and 153. For example, when the first detection area 151 of the first through third detection areas 151, 152, and 153 is the closest to the target area 170, it is determined that a contribution rate of the first detection spectrum S1 of the first through third detection spectrums S1, S2, and S3 is the highest. Accordingly, the contribution rate a of the contribution rates α, β, and γ may have the highest value. As such, the contribution rates α, β, and γ at which the first through third detection spectrums S1, S2, and S3 respectively contribute to the target spectrum ST may be determined by the distances d1, d2, and d3 between the target area 170 and the first through third detection areas 151, 152, and 153, and thus the target spectrum ST of the target area 170 that is located at the specific position to be analyzed may be obtained by using linear combination of Equation 1.

Figure 5:
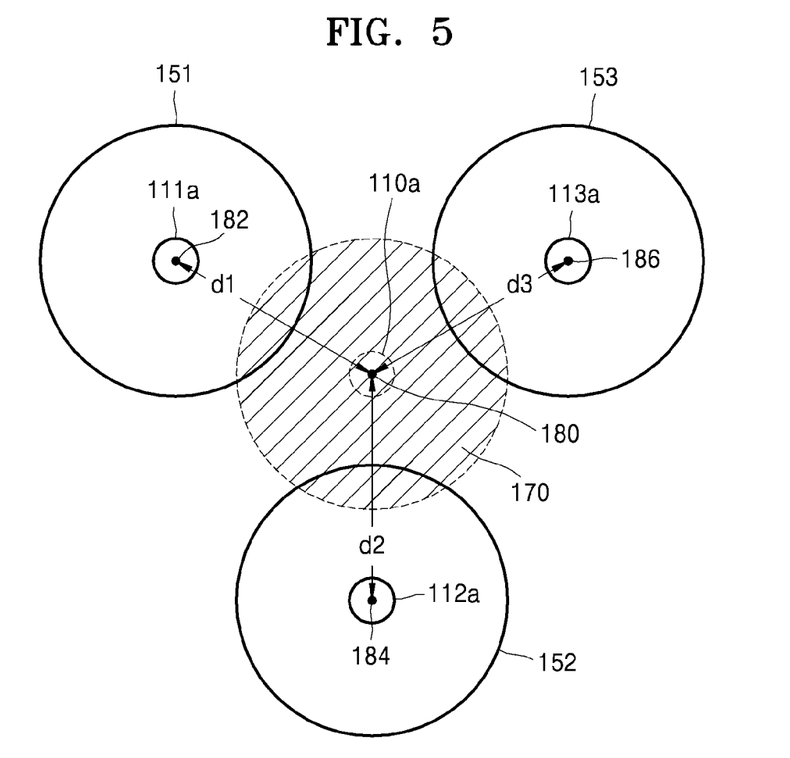
FIG. 5 is a plan view illustrating a state in which the detection areas and the target area are arranged, according to an exemplary embodiment.

Operations of calculating the target spectrum ST according to arrangements of the first through third detection areas 151, 152, and 153 and the target area 170 are described below with reference to FIG. 5. FIG. 5 is a plan view illustrating a state in which the first through third detection areas 151, 152, and 153 and the target area 170 are arranged, according to an exemplary embodiment.

Referring to FIG. 5, the first through third detection areas 151, 152, and 153 are two-dimensionally arranged to be spaced apart from one another. The first through third detection areas 151, 152, and 153 are arranged in an equilateral triangular shape, and the target area 170 is located at a center of the equilateral triangular shape. Accordingly, the target area 170, e.g., the center point 180, is spaced apart by the same distance from the first through third detection areas 151, 152, and 153, e.g., the center points 182, 184, and 186. That is, the distance d1 between the target area 170 and the first detection area 151, the distance d2 between the target area 170 and the second detection area 152, and the distance d3 between the target area 170 and the third detection area 153 are the same.

The target spectrum ST of the target area 170 may be calculated as follows by using Equation 1 when the first through third detection areas 151, 152, and 153 and the target area 170 are arranged as shown in FIG. 5.

First, the first through third detection spectrums S1, S2, and S2 of the first through third detection areas 151, 152, and 153 are respectively detected by the first through third detectors 111, 112, and 113.

Next, the contribution rates $\alpha$, $\beta$, and $\gamma$ at which the first through third detection spectrums S1, S2, and S3 respectively contribute to the target spectrum ST are determined by using the relative position information of the first through third detection areas 151, 152, and 153 with respect to the target area 170. For example, when the distance d1 between the target area 170 and the first detection area 151, the distance d2 between the target area 170 and the second detection area 152, and the distance d3 between the target area 170 and the third detection area 153 are the same, the contribution rates $\alpha$, $\beta$, and $\gamma$ at which the first through third detection spectrums S1, S2, and S3 respectively contribute to the target spectrum ST are also the same. Thus, each of the contribution rates $\alpha$, $\beta$, and $\gamma$ in Equation 1 is 1/3. As a result, in the arrangement of FIG. 5, the target spectrum ST of the target area 170 may be calculated as $1/3 \times S1 + 1/3 \times S2 + 1/3 \times S3$.

Figure 6:
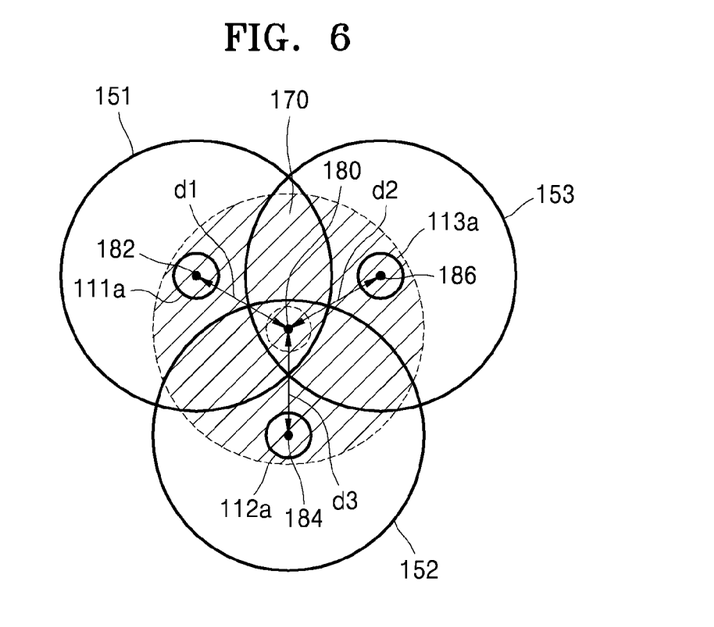
FIG. 6 is a plan view illustrating a state in which the detection areas and the target area are arranged, according to another exemplary embodiment.

FIG. 6 is a plan view illustrating the first through third detection areas 151, 152, and 153 and the target area 170, according to another exemplary embodiment. FIG. 6 is the same as FIG. 5 except that the first through third detection areas 151, 152, and 153 partially overlap with one another.

When at least one of the first through third detection areas 151, 152, and 153 partially overlaps with other detection areas, the first through third detectors 111, 112, and 113 may sequentially detect the first through third detection spectrums S1, S2, and S3 at predetermined intervals. However, an exemplary embodiment is not limited thereto, and the first through third detection spectrums S1, S2, and S3 may be simultaneously detected. Since the distance d1 between the target area 170 and the first detection area 151, the distance d2 between the target area 170 and the second detection area 152, and the distance d3 between the target area 170 and the third detection area 153 are the same in FIG. 6, contribution rates at the first through third detection spectrums S1, S2, and S3 respectively contribute to the target spectrum ST are the same. Accordingly, the target spectrum ST of the target area 170 that is located at the specific position to be measured may be calculated as $1/3 \times S1 + 1/3 \times S2 + 1/3 \times S3$.

Figure 7:
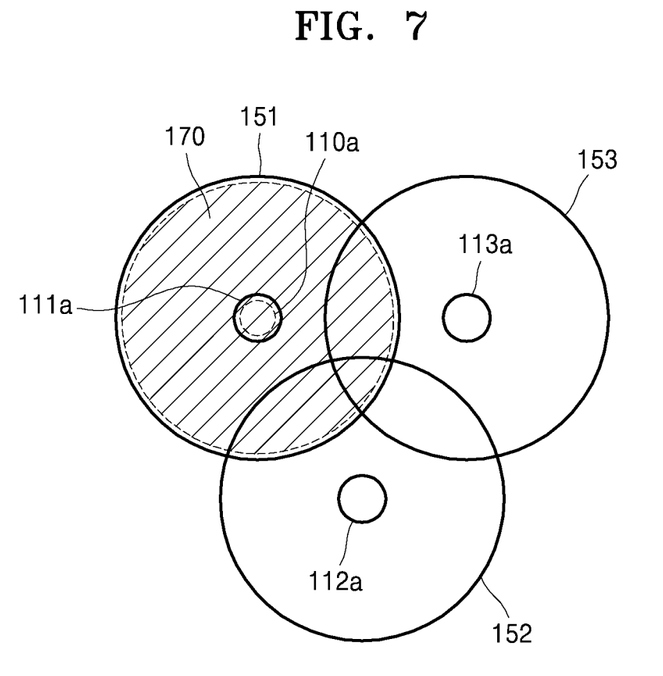
FIG. 7 is a plan view illustrating a state in which the detection areas and the target area are arranged, according to another exemplary embodiment.

FIG. 7 is a plan view illustrating the first through third detection areas 151, 152, and 153 and the target area 170, according to another exemplary embodiment.

Referring to FIG. 7, the first through third detection areas 151, 152, and 153 are two-dimensionally arranged to partially overlap with one another. However, the first through third detection areas 151, 152, and 153 may be provided to be spaced apart from one another. In FIG. 7, the target area 170 entirely coincides with the first detection area 151.

Referring to FIG. 7, the target spectrum ST of the target area 170 may be calculated as follows by using Equation 1. First, the first through third detection spectrums S1, S2, and S3 of the first through third detection areas 151, 152, and 153 are detected by using the first through third detectors 111, 112, and 113. Next, the contribution rates $\alpha$, $\beta$, and $\gamma$ at which the first through third detection spectrums S1, S2, and S3 respectively contribute to the target spectrum ST are determined by using the relative position information of the first through third detection areas 151, 152, and 153 with respect to the target area 170. Because the target area 170 coincides with the first detection area 151, the contribution rate a at which the first detection spectrum S1 contributes to the target spectrum ST is 1, and the contribution rates $\beta$ and $\gamma$ at which the second and third detection spectrums S2 and S2 respectively contribute to the target spectrum ST are 0. As a result, the target spectrum ST of the target area 170 that is located at the specific position to be measured in FIG. 7 is the same as the first detection spectrum S1.

As described above, when the first through third detection areas 151, 152, and 153 are arranged around the target area 170 in various shapes, the target spectrum ST of the target area 170 that is located at the specific position to be measured may be calculated by using the first through third detection spectrums S1, S2, and S3 of the first through third detection areas 151, 152, and 153 and the relative position information of the first through third detection areas 151, 152, and 153 with respect to the target area 170. Although three detection areas are described above, the target spectrum ST of the target area 170 may be calculated when four or more detection areas are two-dimensionally arranged. As described above, when positions of the first through third detection areas 151, 152, and 153 are changed as time passes, the target spectrum ST of the target area 170 that is located at the specific position to be measured may be calculated by compensating for the position change by using the position information of the first through third detection areas 151, 152, and 153.

Referring again to FIG. 4, in operation 205, an analyte of the object 50 in the target area 170 may be analyzed by analyzing the target spectrum ST that is calculated by the information processor 120. That is, the target spectrum ST that is calculated by linearly combining the relative position information of the first through third detection areas 151, 152, and 153 with respect to the target area 170 with the first through third detection spectrums S1, S2, and S3 of the first through third detection areas 151, 152, and 153 may be used to analyze the analyte of the object 50 that is located at the specific position to be measured at a specific point of time.

As described above, according to exemplary embodiments, a target spectrum of a target area may be derived by using position information of detection areas that are located at different positions of an object and detection spectrums of the detection areas. Accordingly, even when positions of the detection areas of the object are changed as time passes, the target spectrum of the target area that is located at a specific position to be measured may be obtained by compensating for the position change. Accordingly, when the object is, for example, the skin of a human, positions of detection areas may be changed as the skin of the human moves. However, a blood glucose spectrum at a specific position may be calculated in real time by linearly combining displacement information of the detection areas with measured blood glucose spectrums of the detection areas.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectroscopy apparatus comprising:
   detectors configured to obtain detection spectrums of respective detection areas that are located at different positions of an object; and
   an information processor configured to obtain a target spectrum of a target area by using position information of the detection areas and the detection spectrums obtained by the detectors,
   wherein the information processor is configured to obtain the target spectrum at a specific position of the target area by applying weights to the detection spectrums of the respective detection areas based on the position information and combining the weighted detection spectrums.

2. The spectroscopy apparatus of claim 1, wherein a relative position of at least one of the detection areas with respect to the target area changes in response an object movement.

3. The spectroscopy apparatus of claim 2, wherein the information processor is configured to calculate the target spectrum by linearly combining the position information of the detection areas with respect to the target area and the detection spectrums.

4. The spectroscopy apparatus of claim 2, further comprising a sensor configured to measure displacements of the detection areas caused by the object movement.

5. The spectroscopy apparatus of claim 1, wherein the detection areas comprise three-dimensional (3D) areas that extend in-depth from a surface of the object.

6. The spectroscopy apparatus of claim 5, wherein the detection areas comprise at least three detection areas that are two-dimensionally arranged.

7. The spectroscopy apparatus of claim 6, wherein the detection areas are spaced apart from one another or partially overlap one another.

8. The spectroscopy apparatus of claim 7, wherein the detectors are configured to measure the detection spectrums of the detection areas simultaneously or sequentially.

9. The spectroscopy apparatus of claim 1, wherein the detectors are configured to measure the detection spectrums by using Raman spectroscopy or near-infrared spectroscopy.

10. The spectroscopy apparatus of claim 1, wherein the detectors are provided adjacent to a surface of the object, and
    each of the detectors comprises an aperture via which each respective detector is configured to receive an optical signal output from a corresponding detection area of the object.

11. A spectroscopy method comprising:
    obtaining detection spectrums of detection areas that are located at different positions of an object with detectors;
    obtaining position information of the detection areas; and
    obtaining a target spectrum of a target area by using the position information of the detection areas and the detection spectrums obtained by the detectors,
    wherein the target spectrum at a specific position of the target area is obtained by applying weights to the detection spectrums of the respective detection areas based on the position information and combining the weighted detection spectrums.

12. The spectroscopy method of claim 11, further comprising analyzing an analyte of the object that is located in the target area, from the target spectrum.

13. The spectroscopy method of claim 11, wherein a relative position of at least one of the detection areas with respect to the target area changes in response to an object movement.

14. The spectroscopy method of claim 13, wherein the obtaining the target spectrum comprises linearly combining the position information of the detection areas with respect to the target area and the detection spectrums.

15. The spectroscopy method of claim 13, wherein the position information of the detection areas is obtained by using a sensor.

16. The spectroscopy method of claim 11, wherein the detection areas comprise three-dimensional (3D) areas that extend in-depth from a surface of the object.

17. The spectroscopy method of claim 16, wherein the detection areas comprise at least three detection areas that are two-dimensionally arranged.

18. The spectroscopy method of claim 16, wherein the detection areas are spaced apart from one another or partially overlap one another.

19. The spectroscopy method of claim 18, wherein the obtaining the detection spectrums comprises measuring the detection spectrums of the detection areas simultaneously or sequentially.

20. The spectroscopy method of claim 11, wherein the obtaining the detection spectrums comprises measuring the detection spectrums by using Raman spectroscopy or near-infrared spectroscopy.

* * * * *